United States Patent [19]

Pellet et al.

[11] Patent Number: 5,523,510

[45] Date of Patent: Jun. 4, 1996

[54] TREATED BOUND FERRIERITE ZEOLITES FOR SKELETAL ISOMERIZATION OF N-OLEFINS TO ISO-OLEFINS

[75] Inventors: Regis J. Pellet, Croton-On-Hudson; Chi-Lin O'Young, Poughkeepsie; John Hazen, Cragsmoor; Alison E. Hadowanetz, Maybrook; James E. Browne, Beacon, all of N.Y.

[73] Assignee: Texaco Inc., White Plains, N.Y.

[21] Appl. No.: 112,920

[22] Filed: Aug. 30, 1993

[51] Int. Cl.[6] .................................. C07C 5/22; C07C 5/27
[52] U.S. Cl. .................................................................. 585/671
[58] Field of Search ...................................... 585/671

[56] References Cited

U.S. PATENT DOCUMENTS

3,565,788  2/1971  Foucher, Jr. et al. .................. 208/111
3,965,209  6/1976  Butter et al. ............................ 585/454
5,157,194  10/1992 Rahmim et al. ....................... 585/671
5,321,194  6/1994  Apelian et al. ......................... 585/671

*Primary Examiner*—Asok Pal
*Assistant Examiner*—E. D. Irzinski
*Attorney, Agent, or Firm*—George J. Darsa

[57] ABSTRACT

A process of converting linear olefins to branched olefins by a skeletal isomerization reaction wherein said reaction is carried out at a temperature of between about 300° C. and about 650° C., under a pressure of between about 0.1 and about 100 atmospheres and a space velocity of said linear olefins of between about 0.1 and about 40 WHSV in the presence of a steamed then acid washed zeolite ferrierite catalyst.

10 Claims, 4 Drawing Sheets

TREATED BOUND FERRIERITE ZEOLITES FOR SKELETAL ISOMERIZATION OF N-OLEFINS TO ISO-OLEFINS

BACKGROUND OF THE INVENTION

This invention relates to olefin isomerization. In one of its more specific aspects, this invention relates to selective isomerization of olefins using a treated bound ferrierite zeolite catalyst.

More particularly, the present invention relates to a process for the preparation of useful hydrocarbons in the presence of a steamed, acid washed bound ferrierite zeolite catalyst in the conversion of n-olefins.

MTBE (methyl tertiary butyl ether) is an effective octane booster. It is made from isobutylene and methanol. The present sources of isobutylene for MTBE production are mainly from by-products of steam or catalytic crackers, and propylene oxide production. However, these supplies are limited. Other possible sources are by isomerization of n-butenes taken from steam or catalytic crackers and by dehydrogenation of isobutane taken from field butanes or produced by dehydroisomerization of n-butane.

Olefin isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

The minimum Brönsted Acid strengths (and equivalents in $H_2SO_4$) required for various acid-catalyzed conversions of hydrocarbons are indicated in the table below.

| Minimum Brönsted Acid Strength Required For The Acid-Catalyzed Conversions of Hydrocarbons | |
|---|---|
| $H_R$ Required | Reaction Type |
| < + 0.8 1.2 wt % $H_2SO_4$ | Cis-trans Isomerization of Olefins |
| < − 6.6 48 wt % $H_2SO_4$ | Double-bond Migration |
| < − 11.6 68 wt % $H_2SO_4$ | Skeletal Isomerization |
| < − 16.0 88 wt % $H_2SO_4$ | Cracking of Alkanes |

It is frequently necessary to convert olefins into other olefins having a different skeletal arrangement. For example, normal butenes are converted into isobutene for polymerization, alkylation, disproportionation or for the production of MTBE. Similarly, normal amylenes must be converted to isoamylenes prior to dehydrogenation to isoprene.

While a number of catalytic materials possess some activity for such a conversion, not all possess sufficient selectivity to be economical. Because the feeds are generally the relatively reactive olefins, many catalysts cause undesirable side reactions such as polymerization or cracking. Consequently, there is a continuing interest in the development of new skeletal isomerization catalysts and processes for isomerizing alkenes to improve efficiencies and to give optimum results for various industrial requirements. A comprehensive review is provided by V. R. Choudhary in "Catalytic Isomerization of n-butene to Isobutene," *Chem. Ind.* Dev, pp. 32–41 (1974).

It is generally known that n-paraffins with, for example, 4 to 7 carbon atoms can be converted to the corresponding isomeric paraffins by using suitable acid catalysts in the temperature range of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding isoolefins except under difficult conditions, for example at very high temperatures and with poor yield. The attempts hitherto described in the literature for the direct isomerization of the skeleton of e.g. n-butene to give isobutene or e.g. of n-pentene to give isopentenes over catalysts arranged in a fixed bed are characterized by initially relatively low yields and selectivities, which diminish and deteriorate further after a short period of operation, often after only a few hours. The deterioration in the yields and selectivities is generally attributed to the loss of actively effective catalyst surface or to the loss of active centers. In addition to this, high coking rates, formation of oligomers and cracking reactions are observed.

As is known, olefins can exist in various isomeric forms. For example, butylenes or butenes exist in four isomers: butene-1, cis-butene-2, its stereo-isomer trans-butene-2, and isobutene; and pentenes exist in six isomers. Conversions between the butenes-2 are known as geometric isomerization, whereas those between butene-1 and the butenes-2 are known variously as position isomerization, double-bond migration, or hydrogen-shift isomerization. These three isomers are not branched and are known collectively as normal or n-butenes. Conversion of the n-butenes to isobutene, which is a branched isomer, is widely known as skeletal isomerization.

Similar, conversions between the 2-pentenes are known as geometric isomerization, whereas those between 1-pentene and the 2-pentenes are known variously as position isomerization, double-bond migration, or hydro-shift isomerization.

Olefins, such as isoamylenes or isobutene have become more and more important recently as one of the main raw materials used in the production of methyl tert-butyl ether (MTBE), an environmentally-approved octane booster to which more and more refiners are turning as metallic additives are phased out of gasoline production. However, processes for the skeletal isomerization of olefins e.g., to produce isobutene, are relatively non-selective, inefficient, and short-lived because of the unsaturated nature of these compounds. On the other hand, positional and skeletal isomerization of paraffins and alkyl aromatics are fairly well established processes, in general utilizing catalysts typically comprising metallic components and acidic components, under substantial hydrogen pressure. Since paraffins and aromatics are stable compounds, these processes are quite successful. The heavier the compounds, in fact, the less severe the operating requirements. Olefins, however, are relatively unstable compounds. Under hydrogen pressure, they are readily saturated to the paraffinic state if a metal component is present in the catalyst.

Furthermore, in the presence of acidity, olefins can polymerize, crack and/or transfer hydrogen. Extensive polymerization would result in poor yields, and short operating cycles. Similarly, cracking would reduce yield. Hydrogen transfer would result in saturated and highly unsaturated compounds, the latter being the common precursors for gum and coke. Any theoretical one step process for producing skeletal isomers of, for example, n-butenes or amylenes, would have to be concerned with the unwanted production of olefin oligomers and cracked products. In addition to these problems, it is well known that skeletal isomerization becomes more difficult as hydrocarbons get lighter.

Skeletal isomerization of olefins is known to be accomplished by contacting unbranched or lightly branched olefins with acidic catalysts at elevated temperatures. The process is generally applicable to the isomerization of olefins having from 4 to about 20 carbon atoms and is especially applicable to olefins having from 4 to about 10 carbon atoms per molecule. The process may be used to form isobutene from normal butylenes, methyl pentenes and dimethyl butenes from normal hexenes, and so forth.

In making the isomerization of these olefins, the acid component, i.e., catalysts, are usually bound together within a matrix or binder generally comprised of alumina, silica, silica-alumina, clay or admixtures thereof to enhance the performance of the acid component (e.g., the yield of product).

Thus, among the objects of this invention are improved processes for the skeletal isomerization of n-butylene and olefins, especially for the isomerization of n-butylene to form isobutylene with treated, bound zeolite catalysts to enhance the performance of bound ferrierite zeolite catalysts.

Other objects and advantages of the invention will be apparent from the following description, including the drawing and the appended claims.

DISCLOSURE STATEMENT

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudhary, V. R., "Fluorine Promoted Catalysts: Activity and Surface Properties", *Ind. Eng. Chem., Prod. Res. Dev.*, 16(1), pp. 12–22 (1977) and U.S. Pat. No. 4,400,574. Numerous catalysts employ a metal or metal oxide in conjunction with a halide-treated metal oxide. For Example, U.S. Pat. No. 4,410,753 discloses isomerization catalysts comprising $Bi_2O_3$ on fluorided alumina and U.S. Pat. No. 4,433,191 discloses skeletal isomerization catalysts comprising a Group VIII metal on halided alumina. Many of the catalysts including halide-treated components require periodic addition of halide materials to maintain catalyst activity; for Example, see U.S. Pat. Nos. 3,558,734 and 3,730,958. An average yield for isobutene of 25 weight percent (within an observed range of 17 to 33 percent) is typically reported when using halided catalysts, based upon a review of various patents cited in this disclosure.

Various techniques have been employed to improve the effectiveness of materials such as alumina and silica as structural isomerization catalysts. For Example, U.S. Pat. No. 3,558,733 discloses methods for activating alumina catalysts with steam, U.S. Pat. No. 4,405,500 discloses catalysts prepared by controlled deposition of silica on alumina and U.S. Pat. No. 4,587,375 discloses a steam-activated silicalite catalyst. In addition, various metal oxides have been used to improve the effectiveness of catalysts based upon alumina, silica or the like.

Zeolitic materials, especially in their hydrogen forms, are known to behave as strong acids. Due to their narrow yet regular pore size they are quite effective in catalyzing olefin polymerization. Unfortunately the pores are soon plugged due to deposition of polymeric materials and frequent catalyst regeneration is necessary to maintain activity.

U.S. Pat. No. 4,503,292 discloses processes for converting n-alkenes to isoalkenes using catalysts containing AMS-1B borosilicate as at least 50 weight percent of the catalyst composition. The borosilicate can be cation-exchanged with hydrogen or metals selected from Groups IB, IIA, IIB, IIIA, VIB and VIII as well as manganese, vanadium, chromium, uranium and rare earth elements. The borosilicate can also be impregnated with metals of Groups IB, IIA, IIB, IIIA, IVB, VB, VIB, VIIB and VIII and rare earth elements.

U.S. Pat. No. 4,435,311 discloses a process for regenerating catalysts containing AMS-1B borosilicates and noble metals by contacting them with water. The process can be carried out during the process of conversion of feedstocks such as alkanes and alkenes to isomerized products such as isoolefins. Similar conversion processes employing catalysts containing such borosilicates are disclosed in U.S. Pat. Nos. 4,777,310; 4,503,282; 4,499,325 and 4,499,326.

Copending U.S. patent application, Ser. No. 07/738,016 discloses normal olefins such as n-butenes can be converted to branched olefin species such as isobutylene by skeletal isomerization over catalysts of borosilicate zeolites having pore sizes of at least about 5 Angstroms and containing boron in the framework structure thereof. The borosilicates have sufficient acidity to catalyze the skeletal isomerization of normal olefins. The catalysts can be used to produce isoolefins for reaction with alcohols in integrated processes to produce alkyl tertiary alkyl ethers such as MTBE.

Copending U.S. application, Ser. No. 07/990,407 discloses that the conversion of normal olefins such as n-butylenes can be converted to branched olefin species such as isobutylene by skeletal isomerization over zeolite-based catalysts having pore sizes of at least about 4.5 Angstroms and a pore structure characterized by intersecting 10-MR and 8-MR channels. The zeolite-based catalysts have sufficient acidity to catalyze the skeletal isomerization of normal olefins. The catalysts can be used to produce isoolefins for reaction with alcohols in integrated processes to produce alkyl tertiary alkyl ethers such as MTBE.

Abandoned U.S. application, Ser. No. 07/990,562 discloses that the conversion of normal olefins such as n-pentene can be converted to branched olefin species such as isopentenes by skeletal isomerization over zeolite-based catalysts having pore sizes of at least about 4.5 Angstroms and a pore structure characterized by intersecting 10-MR and 8-MR channels. The zeolite-based catalysts have sufficient acidity to catalyze the skeletal isomerization of normal olefins. The catalysts can be used to produce isoolefins for reaction with alcohols in integrated processes to produce tertiary amyl methyl ethers such as TAME.

European Patent Application No. 0 501 577 A1 discloses a process for the conversion of a feedstock comprising linear olefins into a product enriched in branched olefins, which process comprises contacting the feedstock with a tectometallosilicate having a ferrierite crystal structure at an olefin partial pressure of more than 0.5 bar.

European Patent Application No. 0 523 838 A2 discloses a process to convert linear alkenes such as butene-1 and butene-2 to methyl branched chain alkenes such as isobutylene using one dimensional, medium pore zeolite catalysts and similar type catalysts such as SAPO's and MeAPOS's. The pore size for the catalyst being greater than 0.42 nm and less than 0.7 nm, preferably with a larger dimension of between 0.5 and 0.6 nm. This pore size allows the branched chain alkenes to form and diffuse out of the catalyst while reducing the formation of unwanted by-products, including dimmers, trimmers, aromatics and coke.

Article by Y. S. Jin et al, STEAMED AND ACID LEACHED TREATMENT [Applied Catalysis 37 (1988) 21–33] discloses a ferrierite type zeolite that is thermally treated under steam at temperatures ranging from 870 to 970K followed by acid leaching with hydrochloric acid solution at 360K. The steamed materials provided no additional interest as acid type catalysts but were more selective for aromatics diffusion, i.e., separating columns or adsorbents.

The use of ferrierite for butene and pentene isomerization is known. The use of acid washed ferrierite for butene isomerization has been described in the article of Y. S. Jin et al., STEAMED AND ACID LEACHED TREATMENT [Applied Catalysis, 37 (1988) 21–33]. The use of steamed ferrierite for pentene isomerization is described in concurrently filed, copending U.S. patent application Ser. No. 08/112,999.

The modification of zeolites by acid washing and steaming is certainly not new. Zeolite acid washing has been described in the open and patent literature as a method to improve acid catalyzed activity. Acid washing removes alkali metal or alkaline earth cations deposited during the zeolite synthesis or commonly present in naturally occurring zeolites; cations are replaced with acidic protons. Thus, U.S. Pat. No. 3,565,788 describes the preparation of a dewaxing catalyst involving acid treatment of the naturally occurring clinoptilolite. No description is given of the effect of acid washing on selectivity or stability in this case.

Several patents disclose the use of steam treatment to modify zeolite catalytic activity. For Example, U.S. Pat. No. 3,965,209 describes the treatment of H-ZSM-5 in 100% steam at 900° C. for 16 hours. The steam treatment reduces the hexane cracking activity of the zeolite and improves selectivity for toluene alkylation. However, there is no reference in U.S. Pat. No. 3,965,209 or open literature related to the combination of steaming and acid washing steps for the purpose of improving ferrierite butene isomerization performance. Nor is there any suggestion that a unique combination of these steps would be particularly effective in improving catalyst properties.

SUMMARY OF THE INVENTION

This invention provides a process of converting linear olefins to branched olefins by a skeletal isomerization reaction wherein said reaction is carried out at a temperature of between about 300° C. and 650° C., under a pressure of between about 0.1 and about 100 atmospheres and a space velocity of said linear olefins of between about 0.1 and about 40 WHSV in the presence of a steamed then acid washed zeolite ferrierite catalyst.

Isomerization conditions include contacting normal olefins with the modified ferrierite zeolite catalyst of this invention at temperatures in the range of about 300° to 650° C., preferably about 400° C. to 580° C. under pressures ranging from about 0.1 to about 100 atmosphere and weight hourly space velocities (WHSV) ranging from about 0.1 to about 40 weight of n-olefin/weight of catalyst per hour. The normal olefins can have from 4 to about 12 carbon atoms, preferably about 4 to 6, and preferably include n-butene.

In a preferred embodiment, the normal olefins are contained in a feedstock which may also contain branched olefins, and the product of the skeletal isomerization step is reacted with an alkanol having from 1 to about 5 carbon atoms (such as methanol or ethanol) under catalytic conditions effective to produce at least one methyl tertiary-alkyl ether, such as methyl tertiary-butyl ether, or ethyl tertiary-butyl ether.

DETAILED DESCRIPTION OF THE INVENTION

The present invention provides a process for isomerizing linear olefins to iso or branched olefins using a modified ferrierite catalyst, said modifications comprising a combination of steaming followed by acid washing treatments. By use of a steamed, acid washed ferrierite zeolite as catalyst in the present process, the yield of isoolefins is significantly increased and catalytic stability is enhanced as illustrated in FIGS. 1 through 4, and the Examples provided below. The modified ferrierite catalyst of the present invention can be prepared by first exchanging the ferrierite with ammonium salts so that the resulting zeolite is substantially in the ammonium exchanged form. This ammonium exchanged zeolite is then steam treated in an atmosphere containing 3 to 100% steam for a period of 1 to 3 hours at temperatures ranging from 500° C. to 700° C. In a preferred embodiment, the steam treatment is conducted in 100% steam atmosphere for one hour at a temperature ranging from 600° C. to 650° C. In order to obtain the benefits of the present process, the ammonium exchanged, then steamed ferrierite must next be acid washed. The acid wash treatment can be accomplished by slurrying the ammonium exchanged, steamed ferrierite in an aqueous solution containing 1 to 10% protic acid, selected from the group consisting of hydrochloric acid, nitric acid and other strong acids at temperatures ranging from 25° to about 100° C. for 15 to 120 minutes. In a preferred embodiment, the acid wash treatment is conducted at 60° to 70° C. for 30 to 50 minutes using about 5% hydrochloric acid and this treatment is repeated two to four times with a water washing step following each acid treatment.

In commercial practice, the zeolite component of the catalyst would be bound together within a matrix comprising alumina, silica-alumina, clay or admixtures thereof. The zeolite component may be modified by steam and acid wash treatments before or after the zeolite is bound with the matrix. Alternatively, a binding step can be provided after the steaming step and before the acid wash treatments. In yet another embodiment, the zeolite is steamed and acid washed then bound with a matrix component and then given additional acid wash treatments. In a preferred embodiment, the zeolite is steamed then acid washed prior to binding. In all embodiments of the present invention the ferrierite modification will consist of a series of steps in which the acid wash treatment follows a steam treatment.

Alumina, silica, and clay are common binders used in the manufacture of zeolite catalysts to provide mechanical strength to form catalyst particles. The binder is usually assumed to be essentially an inert component of the catalysts. The alumina which is used for the matrix material for the catalyst system of the present invention can be any suitable grade of crystalline or amorphous alumina which is substantially inert.

Silica-alumina materials which can be used as binders can be prepared in the same manner as amorphous silica-alumina catalysts, e.g., by adding the zeolite component to a silica-alumina slurry, spray drying, washing the product and drying. Optionally, a clay diluent can be present in the silica-alumina slurry. Such matrixes can be prepared by admixing colloidal alumina (boehmite) and colloidal silica, allowing the matrix properties to vary over a wide range from catalytically inert to active. The activity, thermal stability, surface area and pore distribution of the matrix can be controlled by varying the amounts and particle size distributions of the respective colloids. Further guidance for the preparation of zeolite catalysts containing high porosity matrixes such as silica-alumina can be found in the section by Magee and Blazek on "Zeolite Cracking Catalysts" in ACS Monograph 171, *Zeolite Chemistry and Catalysts* (J. Rabo, Ed.; Am. Chem. Soc., Wash., D.C. 1976).

The zeolite can also be composited with a porous clay matrix material which has suitable binding properties and is resistant to the temperature and other conditions employed in the process. The composite is then calcined to confer the required physical strength. Naturally occurring clays can be composited with the zeolite and these clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie, McNamee-Georgia and Florida clays and others in which the main mineral constituent is halloysite, kaolinite, dickite, nacrite or anauxite. Other clays may also be found to be suitable for use in the present process.

The amount of clay or other matrix material relative to zeolite in the composite will determine, to a certain extent, the physical strength of the final catalyst, especially its attrition resistance and crushing strength. The mechanical properties of the catalyst can therefore be modified by appropriate choice of matrix/zeolite ratio, with greater amounts of matrix generally conferring better mechanical properties. On the other hand, larger amounts of matrix mean that less of the zeolite with its desired, attendant properties will be available to participate in the eventual reaction. A balance will therefore be struck, in most cases, between activity and mechanical properties. Normally, the amount of matrix material will not exceed 50 percent by weight of the composite and in most cases it will not exceed 40 percent by weight and may be lower, e.g. 25 percent by weight or even 15 percent by weight.

The zeolite may conveniently be composited with the clay or other matrix materials by forming an aqueous slurry of the zeolite with the matrix material, spray drying the slurry to form micro-spheres and then calcining. Alternatively, extrudates, pellets and beads can be formed from matrix and zeolite mixtures.

The mixing and homogenizing steps which may be used in the preparation of the zeolite-matrix mixtures are conventional and need not be described; the spray drying may also be carried out in the conventional manner.

The skeletal isomerization processes of this invention are carried out by contacting the feed with the catalyst, using any suitable contacting techniques, at temperatures at which skeletal isomerization of the feed of olefins occurs. The feed is preferably maintained in the vapor phase during contacting. The reactor temperature is preferably in the range of about 300° to about 650° C., more preferably about 400° to about 500° C. The weight hourly space velocity (WHSV) is not narrowly critical but will generally be within the range of about 0.1 to about 40 $hr^{-1}$, preferably from about 1 to about 20 $hr^{-1}$. Any convenient pressure can be used, with the lowest practical pressure preferred in order to minimize side reactions such as polymerization. Preferred pressures are within the range of about 0.1 to about 10 atmospheres, more preferably about 1 to about 4 atmospheres.

The isomerization feedstock contains at least one alkene. The alkenes may have terminal or internal double bonds. Butene feedstocks may contain 1-butene, 2-butene or mixtures thereof. Examples of other normal alkenes which are useful feedstocks are 1- and 2-pentenes; 1-, 2- and 3-hexenes; 1-, 2-, and 3-heptenes; and 1-, 2-, 3-, and 4-octenes.

Particular feedstocks contemplated for use in the present process are fractions containing butenes, e.g., n-butenes. Isobutene present in such fractions is commonly converted by catalytic reaction with methanol to produce methyl tertiary-butyl ether ("MTBE"). MTBE is separated by distillation, leaving a residual ($C_4$) cut. Isobutene present in such fractions may also be oligomerized to produce oligomers which are then separated, again leaving a residual $C_4$ cut. In either MTBE production or oligomerization, a mixture of n-butenes and isobutene remains in the residual material. It is desirable to produce additional isobutene from the residual material and return the isobutene for further conversion by the reactions mentioned above.

The isomerization feed stream can contain inert gaseous diluents (e.g. paraffins, $N_2$, steam, etc.). The diluent may be present in any desired proportion, e.g., up to about 80 weight percent of the feed stream. Hydrogen can be present in the feed stream in addition to such diluents, and with or without steam can have beneficial effects on the product yield and selectivity.

Selection of isomerization conditions is dependent on the olefins to be isomerized. In general, lower temperatures are used for feeds containing larger olefin molecules. Depending on the specific skeletal isomerization catalysts chosen to carry out the steps of the invention, any suitable reaction technique can be utilized, such as fixed bed reaction, fluidized bed reaction, liquid phase batch and continuous operations, and the like. Conventional methods can be used to separate the materials present in the reaction effluent, including fractionation, crystallization, adsorption, and the like. Fractionation is generally preferred. Saturated materials which accumulate in the system can easily be removed by suitable techniques well known in the art.

In one aspect of the process according to the present invention, the conversion of n-alkenes into isoalkenes, preferably butylenes into isobutylene, almost up to the establishment of thermodynamic equilibrium is achieved. This equilibrium, between 400° to 500° C., is about 40 to 45 percent by weight in the case in which the pure system of the n-butylenes and isobutylene is considered. This equilibrium may not be achieved in the case of a single contact of the mixture to be employed according to the present invention with the catalyst to be employed during the present process. However, in a particular variant of the process, the product stream leaving the catalyst bed can be divided up, and only one part is directly conveyed to the working-up process, while the other part is again conducted over the catalyst bed. This division of the product stream for recycling can vary within wide limits, for example between the proportions of 1:9 to 9:1 of worked-up or recycled material. In this process, a high recycling rate implies a smaller throughput, relative to a constant catalyst charge and constant remaining reaction conditions, but brings a desired shift of the spectrum of components in favor of the isoalkene, e.g. of the isobutene, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the present invention, the process can, in general, be operated without any recycling rate. This can be optimized by simple preliminary experiments.

According to the present invention, a preferred embodiment of the invention is directed to an integrated process for skeletal isomerization of normal butenes to produce isobutene, which is then used in the production of methyl tertiary-butyl ether (MTBE). Streams of a mixed butene feedstock and methanol are reacted in a MTBE synthesis reactor, the methanol reacting with the isobutene in the mixed feedstock to form MTBE which is then taken off via an exit line. The MTBE synthesis reactor acts as a $C_4$ separation unit, since the methanol reacts selectively with isobutene. Other mixed olefin streams could be treated in the same manner, e.g. reacting methanol with isoamylenes to form tertiary-amyl methyl ether (TAME). Other alcohol streams could be employed in a similar manner; e.g., reacting ethanol with mixed butenes to form ethyl tertiary-butyl ether (ETBE). The alcohol stream can contain at least one alkanol having from 1 to about 5 carbon atoms. Depending upon whether streams containing substantially single alcohols or mixtures thereof are employed, the corresponding alkyl tertiary-alkyl ether or mixtures containing various groups can be produced.

The product raffinate stream is fed to a skeletal isomerization unit wherein a catalyst of the present invention is employed to isomerize normal butenes and/or butanes to isobutene for recycle to the MTBE reactor via recycle line. Hydrogen or steam can be introduced into isomerization section to improve reactor performance. Saturated species which are unsuitable for isomerization can be separated and purged from the raffinate via an exit line, or as part of the by-products ($C_1$–$C_3$ gases and polygas) which are separated from the isomerization section via other exit lines.

Such an integrated process permits a mixed feed stream of butenes (or other alkanes and/or alkenes) to be used most effectively in the production of MTBE (or other alkyl tertiary-alkyl ethers) via the skeletal isomerization of alkenes and recycle to the MTBE reactor. The skeletal isomerization processes and catalysts of the present invention are of course useful in processing feed streams containing normal alkenes from a variety of sources.

The present invention provides a process and catalyst for isomerizing butene. The catalyst used consists of ferrierite, modified by a unique combination of steaming and acid washing steps. Surprisingly, the combination of treatments and very importantly the order of treatment steps has a significant and beneficial effect on performance and stability.

In the present skeletal isomerization for the conversion of linear olefins (e.g., n-butene) the reaction is carried out at a temperature of between about 300° and about 700° C., preferably from about 400° C. to about 500° and most preferably from about 400° C. to about 450° C. The pressure under which the reaction is carried out ranges from about 0.1 to about 100 atmospheres. And, the space velocity under which the reaction is carried out is between about 0.1 and about 40 WHSV.

Spent catalysts can be regenerated by heating in a similar oxygen-containing gas, such as air, at temperatures ranging from about 200° C. to about 700° C. This process is significantly simpler than that required for halided metal oxide catalysts, in which a separate step of replacing the halide component must be employed.

EXAMPLES

The present invention is further illustrated by reference to the following Examples which will demonstrate the significantly improved start-of-run selectivity and hydrothermal stability of ferrierite that has been steamed then acid washed prior to use. Comparative Examples will show that neither steam nor acid wash treatments alone can provide the same benefits as the combined treatment. Comparative Examples will also show that the order in which the combined treatments are applied is critical to achieving the advantages of the present invention. Thus, a comparative catalyst which has been acid washed then steamed lacks the improved performance of the catalysts of the present invention which were first steamed then acid washed prior to use.

Example 1

FERRIERITE BASED CATALYST
(COMPARATIVE)

A commercially supplied ferrierite powder was used to prepare an ammonium exchanged, alumina bound ferrierite extrudate. The commercial zeolite, HSZ-720KOA, [manufactured and sold by TOYO SODA USA Inc. of Atlanta, Ga.] was analyzed to contain 84.7% $SiO_2$, 8.16% $Al_2O_3$, 1.5% $Na_2O$ and 5.6% $K_2O$. The ammonium exchanged form was prepared by a double ion exchange with ammonium nitrate solution. Specifically, 1000 grams of ferrierite powder were added to a solution containing 1000 grams of ammonium nitrate and 2500 grams of water. The slurry was heated to 90° C. and stirred continuously for 2 hours at temperature. The exchange solution was removed by filtration and a fresh solution of identical composition was added to the ferrierite powder. The new slurry was again heated to 90° C. and stirred for 2 hours at temperature. Following exchange the powder was water washed extensively then dried overnight at 120° C. This ammonium exchanged ferrierite powder served as an intermediate to this and subsequent preparations. Alumina bound extrudates were prepared by mixing 8 grams of the ammonium exchanged ferrierite powder (containing about 13% volatiles) with 2.01 grams of DISPAL, a boehmite alumina commercially available from Vista Chemical Company, of Houston, Tex. (80% $Al_2O_3$) and 13.63 grams of water. The resulting paste was extruded to obtain 1/16 inch pellets which were dried at 120° C. overnight and calcined at 600° C. for 2 hours in dry air. This comparative catalyst was estimated to contain about 81% ferrierite and 19% alumina binder.

Example 2

FERRIERITE BASED CATALYST (COMPARATIVE)

A second batch of ammonium exchanged, alumina bound ferrierite extrudates were prepared using a portion of the ammonium ferrierite prepared in Example 1 above. Thus, 160 grams of ammonium ferrierite, were mixed with 40 grams of DISPAL and 350 grams of water. The resulting paste was extruded to obtain 1/16 inch pellets and dried overnight at 120° C. This procedure was repeated an additional three times and the resulting batches were combined to obtain about 800 grams of dried extrudates, the comparative catalyst of this Example. These extrudates were prepared to contain about 80% zeolite and 20% binder.

Example 3

STEAMED FERRIERITE BASED CATALYST (COMPARATIVE)

In order to demonstrate the effect of steam modification, 3 grams of the catalyst of Example 2 were heated to 600° C. in air. At 600° C., the air flow was saturated with water prior to passage over the catalyst bed. The catalyst was kept at these conditions for 2 hours and then cooled in dry air to provide the catalyst of this Example.

Example 4

ACID WASHED FERRIERITE CATALYST (COMPARATIVE)

An ammonium exchanged ferrierite was prepared in a manner similar to that used in the above Examples 1 and 2. Next, 50.3 grams of this material were slurried in 750 grams of 5% hydrochloric acid solution at 65° C. for 42 minutes. This material was filtered and water washed, dried at 120° C. overnight and calcined at 600° C. for 4 hours. The acid washing procedure was repeated one more time on 30 grams of this material to obtain a twice acid washed ferrierite powder. The twice acid washed powder was split into two batches and used to prepare two comparative acid washed catalysts of this Example.

Example 4(A)

The catalyst of this Example was prepared by providing a third acid wash to a portion of the twice acid washed powder. The product was then bound using DISPAL alumina, extruded to 1/16 inch pellets and dried and calcined as described above. The resulting catalyst was prepared to contain 75% of triply acid washed ferrierite and 25% alumina binder.

Example 4(B)

A second portion of twice acid washed ferrierite was bound with DISPAL alumina and extruded to obtain 1/16 inch pellets. These extrudates were calcined, subjected to a third acid wash similar to the ones applied above except that bound extrudates were washed in this Example whereas in the preceding Example ferrierite powder was given a third acid wash. The washed material was then dried and calcined again. This is the catalyst of this Example and was also prepared to contain 75% ferrierite and 25% binder.

Example 5

ACID WASHED, STEAMED FERRIERITE CATALYST (COMPARATIVE)

Triply acid washed ferrierite extrudate of Example 4B above were subjected to an additional steaming as described above in Example 3. The steaming was performed for 2 hours at 600° C. in water saturated air to provide the comparative catalyst of this Example.

Example 6

STEAMED, ACID WASHED FERRIERITE CATALYST (ILLUSTRATIVE)

A catalyst of the present invention was prepared by first steaming an ammonium exchanged ferrierite powder, followed by acid washing. The steamed acid washed powder thus produced was bound, extruded, dried and calcined to obtain the finished catalyst. Specifically, an ammonium exchanged ferrierite was prepared as in Example 1. Next, 15 grams of this material was place in a vertical quartz tube and heated to 600° C. in flowing air. At 600° C., air flow was stopped and was replace with a water supply at 0.5 cc/minute. The ferrierite powder was maintained at 600° C. for 1 hours under 100% steam atmosphere then cooled in air. 11.7 grams of the steamed powder were slurried in 210 grams of 5% hydrochloric acid solution at 60° C. for 40 minutes. The acid washed ferrierite was filtered and reslurried in water at room temperature for an additional 20 minutes. After water washing, the powder was reslurried in 210 grams of fresh 5% HCl at 60° C. for 40 minutes then filtered, water washed and dried at 120° C. overnight. 12.73 grams of the twice acid washed powder (partially dried) thus prepared was mixed with 4.24 grams of DISPAL alumina and 15.5 grams of water and extruded to obtain 1/16 inch pellets which were dried and calcined at 600° C. for 2 hours in air. This steamed, acid washed catalyst was prepared to contain about 78% ferrierite and 22% alumina binder to provide the catalyst of this Example.

Example 7

STEAMED, ACID WASHED FERRIERITE CATALYST (ILLUSTRATIVE)

Another catalyst exemplifying the present invention was prepared as follows. 1.1 Kg of commercially supplied ferrierite powder, HSZ-720KOA, were ammonium exchanged by slurrying in a solution of 1.1 Kg of ammonium nitrate dissolved 2.75 Kg of water at 90° C. for 2 hours. After two hours the spent exchange solution was decanted and a fresh ammonium nitrate solution of identical composition and amount was added to the exchanged solids. The mixture was slurried at 90° C. for an additional 2 hours. Again the spent solution was decanted and the twice exchanged solids were water washed and dried overnight at 110° C. Ammonium exchanged ferrierite thus prepared was steamed by placing approximately 200 grams of this powder in a vertical quartz tube, which was heated to 640° C. in flowing air. Once at temperature, the air flow was interrupted and water was pumped into the tube at a rate of 2.8 ml/min to generate steam in-situ. The water flow rate and temperature were maintained for 1 hour and then the steamed powder was cooled in dry air. This procedure was repeated 3 additional times using about 200 grams of fresh ammonium exchanged ferrierite. Steamed batches of ferrierite were combined. Next 610 grams of the combined, steamed ferrierite batches were washed with an acid solution containing 811 grams of hydrochloric acid and 5200 grams of water maintained at 64° C. for 40 minutes. The wash solution was then decanted and replaced with equivalent amount of fresh acid solution. In this manner, the wash procedure was repeated until the steamed ferrierite powder was triply acid washed. The acid washed powder was then water washed with three portions of 5200 grams of water and dried overnight at 120° C. Next 6.9 grams of the steamed, acid washed ferrierite were combined with 5 grams of DISPAL alumina and 11.1 grams of water. The resulting paste was extruded to obtain 1/16 inch extrudates which were dried at 120° C. overnight. This catalyst was prepared to contain 60% steamed acid washed ferrierite and 40% alumina binder after calcination to provide the catalyst of this Example.

Example 8

STEAMED, ACID WASHED FERRIERITE CATALYST (ILLUSTRATIVE)

Another steamed, acid washed catalyst was prepared in order to demonstrate additional procedures by which the advantages of the present invention can be achieved. To this end alumina bound, ammonium ferrierite extrudates, prepare as described in Example 2 above were steamed by placing 15 grams of extrudates in a vertical quartz steamer which was then heated to 600° C. in flowing air. At temperature, the air flow was replaced with water flowing into the tube at 0.5 ml/min to generate steam in-situ. The catalyst was maintained at temperature in steam for 1 hour then cooled in dry air. The steamed extrudates were then acid washed by mixing 13 grams of extrudates with 210 grams of 5% HCl solution at 70° C. for 40 minutes. The spent acid solution was decanted and the extrudates were washed in water for 40 minutes at room temperature. Water was decanted and the extrudates were given a second acid wash with 150 grams of 5% HCl solution at 70° C. for forty minutes. Again the extrudates were water washed, then dried overnight at 120° C. and calcined at 600° C. for 4 hours to provide the steamed then twice acid washed catalyst of this Example.

Example 9

STEAMED, ACID WASHED, STEAMED FERRIERITE CATALYST (ILLUSTRATIVE)

In order to demonstrate the superior hydrothermal stability of the present catalysts, 3.5 grams of the catalyst of Example 6 were heated to 600° C. in air. At 600° C., the air flow was saturated with water prior to passage over the catalyst bed. The catalyst was kept at these conditions for 2 hours and then cooled in dry air to provide the catalyst of this Example.

The success of the present invention depends not only on the application of the appropriate treatment steps but also on the order in which these steps are applied. Below, Table I summarizes the key steps involved in preparing the catalysts of the present invention as described above. It will also aid in distinguishing those steps and their order of application from the comparative catalyst preparations also presented above. Catalysts of Examples 6, 7, 8 and 9 are catalysts of the present invention. An essential feature of all of these materials is that a steam treatment has been applied prior to an acid wash step. It can be seen from these Examples and from Table 1 that the ordering of additional preparative steps such as the binding step are not critical to achieving the advantages of the catalysts of the present invention. Furthermore, and very importantly, additional steam treatment following the essential steam-acid wash combination will be seen to have little effect on the performance of the catalysts of the present invention.

TABLE I

PREPARATION OF COMPARATIVE AND ILLUSTRATIVE CATALYSTS

| Catalyst of Example | STEP 1 | STEP 2 | STEP 3 | STEP 4 | STEP 5 |
|---|---|---|---|---|---|
| 1 | NH4+ Ex. | Binding | | | |
| 2 | NH4+ Ex. | Binding | | | |
| 3 | NH4+ Ex. | Binding | Steam (600° C.) | | |
| 4A | NH4+ Ex. | A. Wash, (3X) | Binding | | |
| 4B | NH4+ Ex. | A. Wash. (2X) | Binding | A. Wash (1X) | |
| 5 | NH4+ EX. | A. Wash (2X) | Binding | A. Wash (1X) | Steam (600° C.) |
| 6 | NH4+ Ex. | Steam, (600° C.) | A. Wash. (2X) | Binding | |
| 7 | NH4+ Ex. | Steam, (640° C.) | A. Wash, (3X) | Binding | |
| 8 | NH4+ Ex. | Binding | Steam, (600° C.) | A. Wash (2X) | |
| 9 | NH4+ Ex. | Binding | Steam (600° C.) | A. Wash, (2X) | Steam, (600° C.) |

Example 10

CATALYST EVALUATION FOR BUTENE ISOMERIZATION

In order to demonstrate the advantages obtained when using catalysts of the present invention, all catalysts described above were evaluated for butene isomerization activity and selectivity as follows. Each catalyst to be evaluated was calcined prior to use and then crushed to obtain a 20/40 mesh fraction. One gram of the fraction was loaded to a 0.5 inch I.D. stainless steel tube reactor. The catalyst was heated to reaction temperature, 420° C. in flowing nitrogen and then a one-to-one mixture of nitrogen (2.g per hour) and 1-butene (5.34 grams/hour) was passed over the catalyst at one atmosphere pressure for 16 to 24 hours. During this period the product stream was analyzed hourly and the conversion and selectivity of the catalyst was monitored by on-line gas chromatographic analysis. Results of the analysis are summarized in FIGS. 1 to 4 and, below, in Table II.

In Table II, below, there is a comparison of the effectiveness of the untreated ferrierite catalyst (FER) with that of:

1. steamed ferrierite (S-FER);

2. acid washed ferrierite (AW-FER);

3. acid washed, steamed ferrierite (AW-S-FER); and 4. steam, acid washed ferrierite (S-AW-FER).

TABLE II

FERRIERITE MODIFICATIONS
(16 Hour Run Averaged Performance)

| CATALYST | FER | S-FER | AW-FER | AW-S-FER* | S-AW-FER |
|---|---|---|---|---|---|
| Example | 1 | 3 | 4A | 5 | 7 |
| CONVERSION | 57.3 | 46.2 | 57.6 | 54.7 | 48.9 |
| ISOBUTENE YIELD | 35.1 | 32.2 | 33.5 | 34.4 | 39.8 |
| ISOBUTENE SELECTIVITY | 61.4 | 69.6 | 58.2 | 63 | 81.3 |

*Abbreviated Run, 7 Hour Run Averaged Data

CONCLUSIONS

Figure 1:
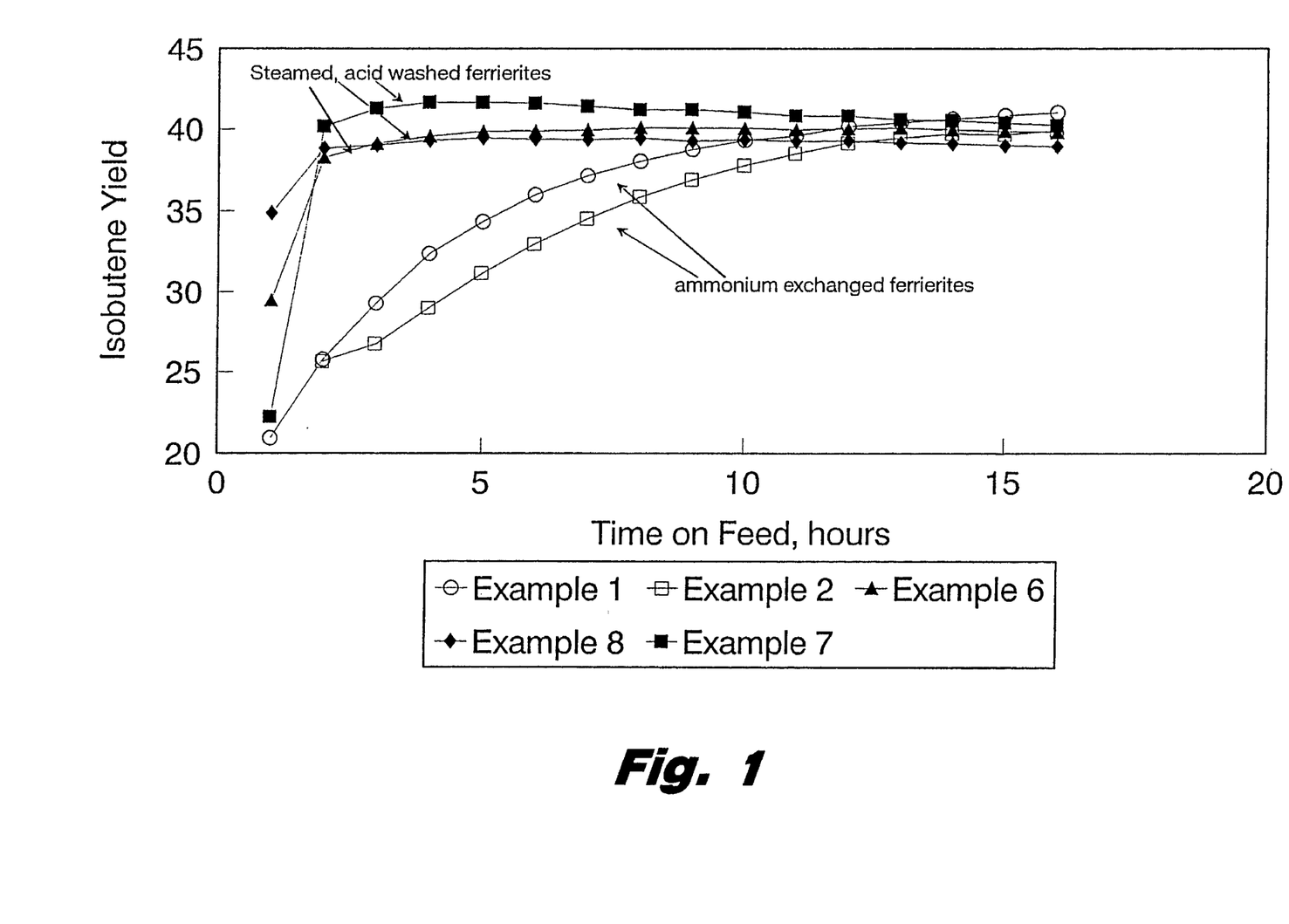
FIG. 1 is a graph showing the isobutene yield versus the Time on the feed for several of the Examples where the steamed, acid washed ferrierite zeolite catalysts are compared to ammonium exchanged ferrierite zeolite catalysts.

FIG. 1 compares isobutene yields achieved with unmodified ferrierites from Examples 1 and 2 with three catalysts of the present invention which have been steamed then acid washed as per Examples 6,7 and 8. Yields are presented as a function of time on feed. Initial yields achieved with the unmodified ferrierite catalysts are low, about 20 to 25%, and only after several hours on feed do they approach the maximum observed during the course of the run. By comparison, the steamed acid washed ferrierites approach maximum yield by the second hour of the run and essentially maintain that maximum yield over the course of the 16 hour test. Obviously, a significantly higher run average yield is possible with the steamed acid washed catalysts.

Figure 2:
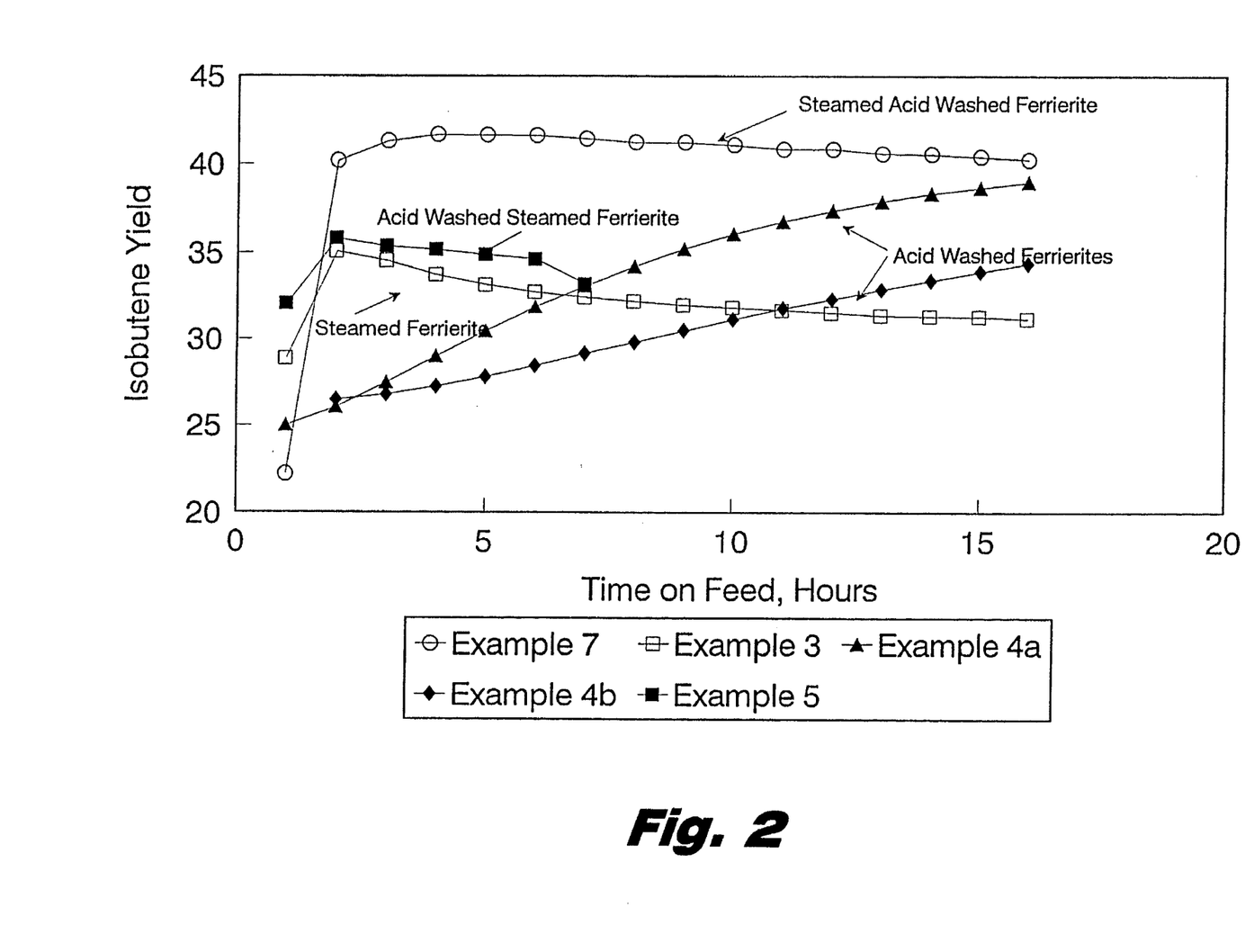
FIG. 2 is a graph showing the Isobutene yield versus the Time on feed for several Examples where the steamed, acid washed ferrierites are compared with: acid washed, steamed ferrierites; acid washed ferrierite; and steamed ferrierites.

FIG. 2 plots isobutene yields as a function of time on feed for the other comparative catalysts and again for a steamed acid washed formulation of the present invention. The figure shows that neither steaming nor acid washing alone result in a catalyst with the high start of run yields achieved with the steamed-acid washed ferrierite. Note also that the acid washed then steamed ferrierite exhibits yields inferior to the steamed then acid washed catalysts of the present invention. These results indicate that not only are both treatment steps essential but that the steaming step must precede the acid wash step if the maximum selectivity catalyst is to be obtained.

As mentioned before, the improved start-of-run yield obtained with catalyst of the present invention represents a significant increase in the run average yield obtained when run cycles are of limited duration. Table 2 summarizes the run average performances of the catalysts of the present invention as well as those of the comparative Examples described above. Note that none of the comparative catalysts approach the run average selectivity, greater than 81% for the steamed acid washed catalyst.

Catalysts of the present invention have another key advantage over the comparative catalysts in that they are able to withstand the degradive effects of subsequent steam treatments. The ability of isomerization catalysts to withstand hydrothermal treatment provides an indication of how well these catalysts will perform following multiple oxidative coke burning regenerations. It is well know that regeneration of spent catalysts by combustion of carbon deposits at elevated temperatures generates water as a combustion product. This water at the elevated temperatures at which the coke burn occurs subjects the regenerated catalyst to degradive hydrothermal conditions which reduce catalyst performance after multiple cycles. The effects of the steam treatments described in Examples 3 and 9 are informative in that they simulate the degradive effects of steam on the comparative catalysts as well as on the catalysts of the present invention.

Figure 3:
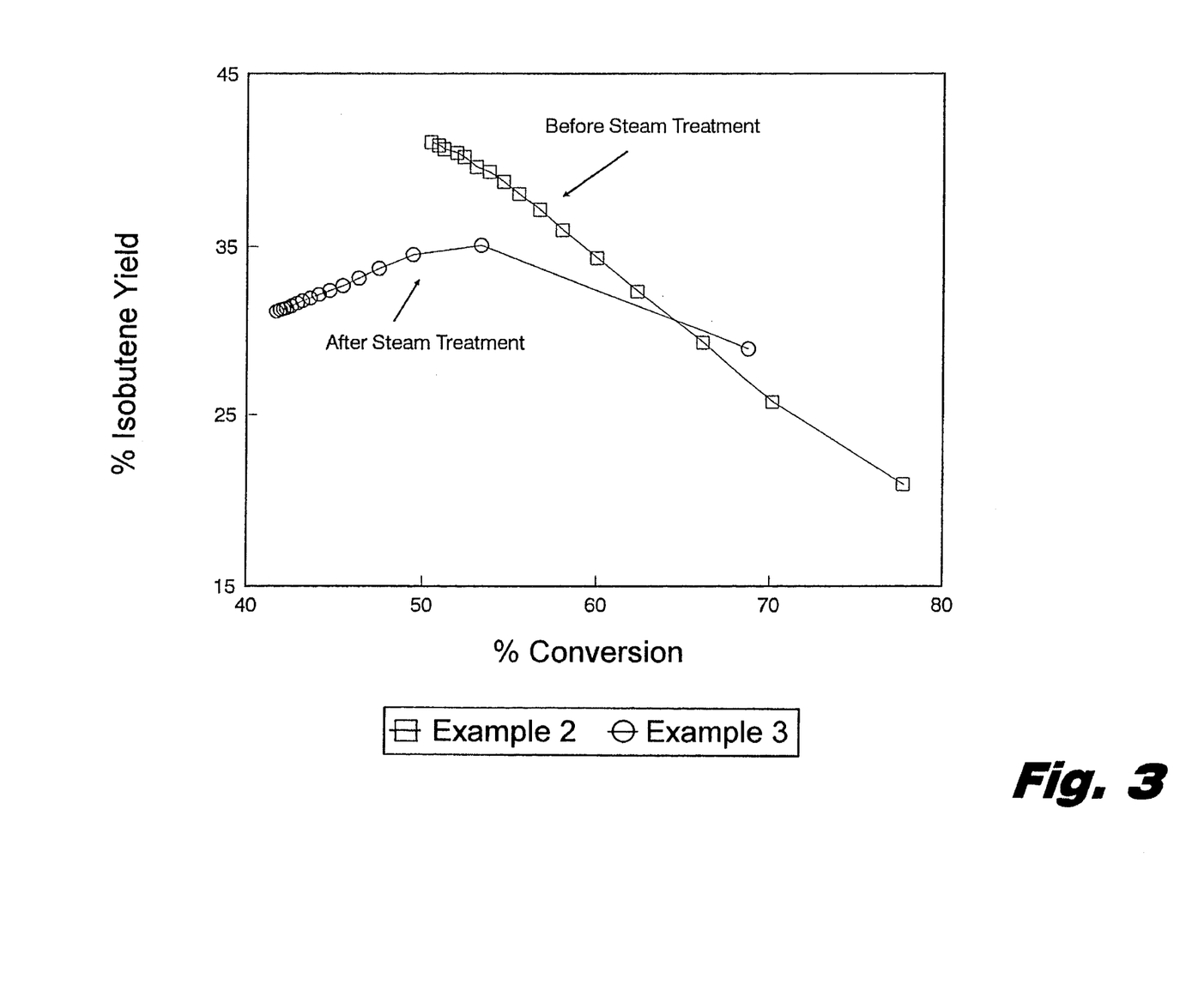
FIG. 3 is a graph showing the effect of steam treatment on ferrierite zeolite catalysts in the conversion of isobutenes to butenes.
Figure 4:
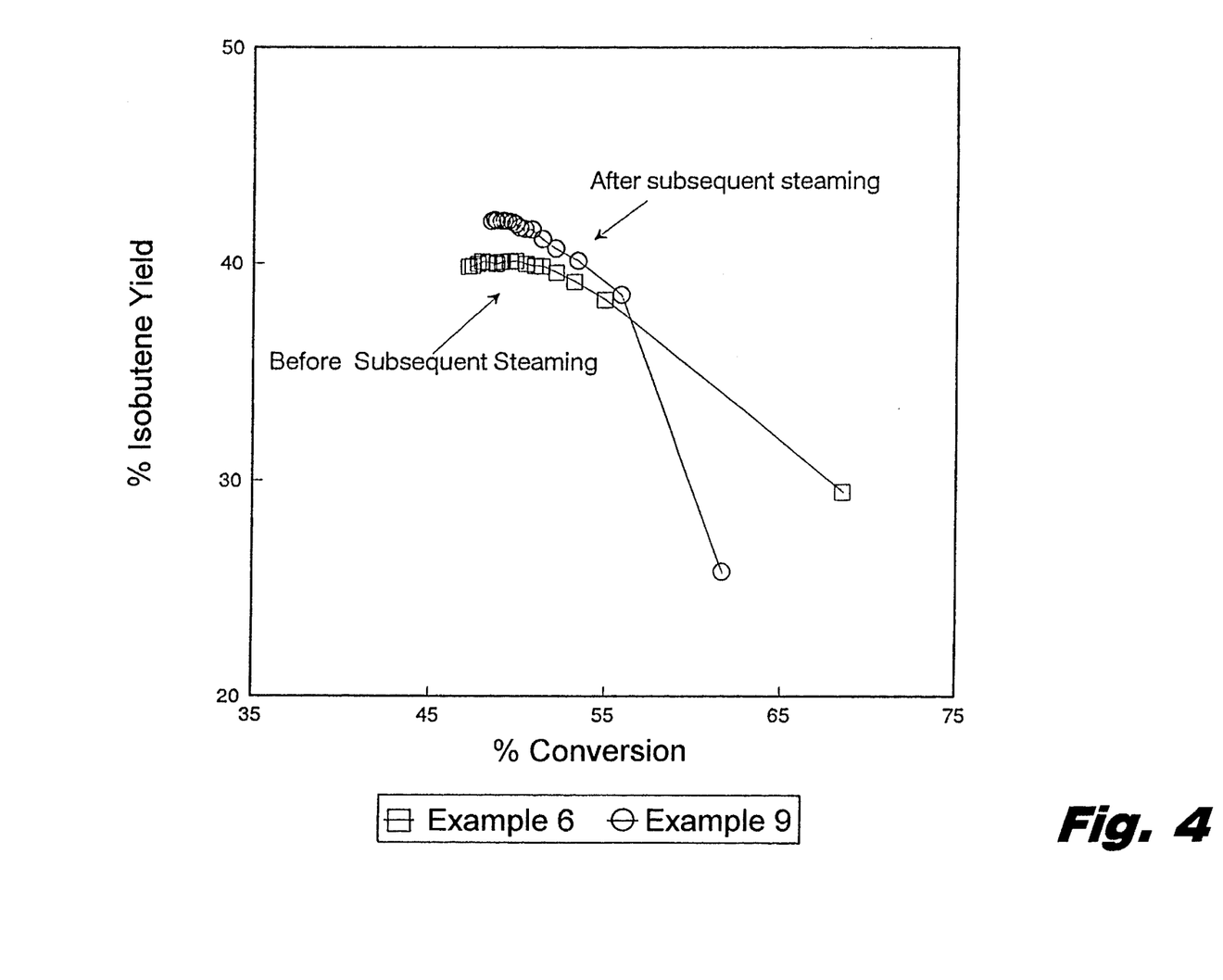
FIG. 4 is a graph showing the effect of steam treatment on steamed acid washed ferrierite zeolite catalysts in the conversion of isobutenes to butenes.

These effects are demonstrated by FIGS. 3 and 4. Here the performance of fresh and steamed catalysts are compared. FIG. 3 plots isobutene yield against conversion for the comparative, ferrierite before and after high temperature steam treatment described in Example 3. FIG. 4 plots similar data for catalysts of the present invention before and after similar steam treatment as described in Example 9. From FIG. 3, it can be seen that selectivity to isobutene is severely degraded by the 600° C. steam treatment of unmodified ferrierite. Similar treatment of steamed, acid washed ferrierite of the present invention is seen to have no deleterious effect on selectivity. As seen in FIG. 4, the performance before and after degradive steam treatment is identical within the limits of experimental error. The improved steam stability exhibited by catalysts of the present invention should represent long term stability and resistance to degradation following several cycles of use and regeneration.

Superior butene isomerization performance is achieved using a novel modified ferrierite catalyst. Advantages of the present invention include very significantly improved initial performance and improved hydrothermal stability, regenerability and shelf life. The effective modifications comprise a unique combination of steaming and acid wash steps that render the ferrierite highly resistant to damage in subsequent use.

We claim:

1. A process for the skeletal isomerization of a linear olefin to provide a branched olefin product which comprises contacting a linear olefin under skeletal isomerization conditions with, as skeletal isomerization catalyst, ferrierite which has previously been steamed and thereafter acid washed.

2. The process of claim 1 wherein the skeletal isomerization conditions include a temperature of between about 300° C. and 700° C., a pressure of between about 0.1 and about 100 atmospheres and a space velocity of said linear olefin of between about 0.1 and about 40 weight hourly space velocity.

3. The process of claim 1 wherein the linear olefin is contacted with, as skeletal isomerization catalyst, ferrierite which has previously been steamed at about 500° C. to about 700° C. in an atmosphere containing 3 to 100% steam for a period of 1 to 3 hours and thereafter acid washed.

4. The process of claim 3 wherein the linear olefin is contacted with, as skeletal isomerization catalyst, ferrierite which has previously been steamed at about 600° C. to about 650° C. in an atmosphere containing 100% steam and thereafter acid washed.

5. The process of claim 1 wherein the linear olefin is contacted with, as skeletal isomerization catalyst, ferrierite which has previously been steamed and thereafter acid washed with aqueous strong acid.

6. The process of claim 1 wherein the linear olefin is contacted with, as skeletal isomerization catalyst, ferrierite which has previously been steamed and thereafter acid washed with a 1 to 10 weight percent solution of a strong mineral acid at a temperature of from about 25° C. to about 100° C. for from about 15 to about 120 minutes.

7. The process of claim 6 wherein the linear olefin is contacted with, as skeletal isomerization catalyst, ferrierite which has previously been steamed and thereafter acid washed up to four times.

8. The process of claim 3 wherein the linear olefin is contacted with, as skeletal isomerization catalyst, ferrierite which has previously been steamed and thereafter acid washed with aqueous strong acid.

9. The process of claim 3 wherein the linear olefin is contacted with, as skeletal isomerization catalyst, ferrierite which has previously been steamed and thereafter acid washed with a 1 to 10 weight percent solution of a strong mineral acid at a temperature of from about 25° C. to about 100° C. for from about 15 to about 120 minutes.

10. The process of claim 1 wherein the linear olefin is an n-butene and the branched olefin is an isobutene.

* * * * *